United States Patent [19]

Okuda et al.

[11] Patent Number: 4,532,254
[45] Date of Patent: Jul. 30, 1985

[54] INHIBITOR OF ALDOSE REDUCTASE

[75] Inventors: Jun Okuda; Ichitomo Miwa, both of Nagoya; Kazuhiro Inagaki, Okazaki; Tokunaru Horie, Tokushima; Mitsuru Nakayama, Hiroshima, all of Japan

[73] Assignee: Kaken Pharmaceutical Co., Ltd., Tokyo, Japan

[21] Appl. No.: 476,153

[22] Filed: Mar. 17, 1983

[51] Int. Cl.³ ............................................. A61K 31/35
[52] U.S. Cl. .................................... 514/456; 514/866
[58] Field of Search ........................................ 424/283

[56] References Cited
PUBLICATIONS

*Chem. Abstracts,* vol. 78, (1973), 11468V.

Primary Examiner—Frederick E. Waddell
Attorney, Agent, or Firm—Armstrong, Nikaido, Marmelstein & Kubovcik

[57] ABSTRACT

An inhibitor of aldose reductase which contains, as the effective ingredient, a flavone derivative having the following formula:

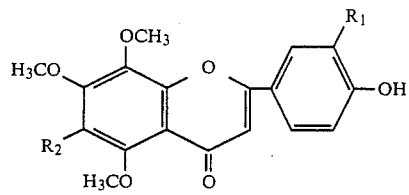

wherein $R_1$ is hydrogen atom or hydroxyl group, $R_2$ is hydroxyl group or methoxyl group or a pharmaceutically acceptable salt thereof, and a pharmaceutically acceptable carrier. The inhibitor is useful for preventing, reducing or treating complications of diabetes.

2 Claims, No Drawings

INHIBITOR OF ALDOSE REDUCTASE

BACKGROUND OF THE INVENTION

The present invention relates to an inhibitor of aldose reductase (hereinafter referred to as "AR") containing a flavone derivative or a pharmaceutically acceptable salt thereof as an effective ingredient.

Complications of diabetes such as cataract and diseases of the retina and the kidney are caused by an unnecessary and harmful accumulation of the corresponding polyols derived from sugars by AR. For instance, sugar cataract is caused by turbidity of a lens which is caused by unnecessary and harmful accumulation of the corresponding sugar alcohols derived from glucose and galactose by AR which exists in a lens of an eyeball. Accordingly, it is essential to inhibit the enzyme activity of AR being a direct cause of the complications as strong as possible in order to effectively prevent, reduce or treat the above complications.

There hitherto have been provided many compounds such as alrestatin and sorbinil as effective ingredients of inhibitors of AR. The most potent example of those inhibitors was quercitrin which is one of flavone derivatives having the following formula (I):

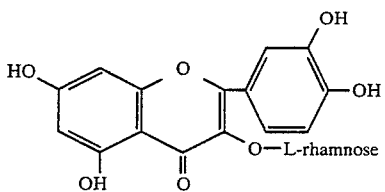

Quercitrin, however, is not potent enough to inhibit AR activity.

As a result of extensive study on dozens of flavone derivatives to find more potent inhibitors of AR by utilizing AR from rat and bovine lenses, it has now been found that 3',4',6-trihydroxy-5,7,8-trimethoxyflavone (hereinafter referred to as "LARI-1"), 4'-hydroxy-5,6,7,8-tetramethoxyflavone (hereinafter referred to as "LARI-2"), 4',6-dihydroxy-5,7,8-trimethoxyflavone (hereinafter referred to as "LARI-3") and 3',4'-dihydroxy-5,6,7,8-tetramethoxyflavone (hereinafter referred to as "LARI-4") and the salts thereof have particularly potent inhibitory activities against AR.

SUMMARY OF THE INVENTION

In accordance with the present invention, there can be provided a pharmaceutical composition having a particularly potent inhibitory activity against AR containing, as the effective ingredient, a flavone derivative having the following formula (II):

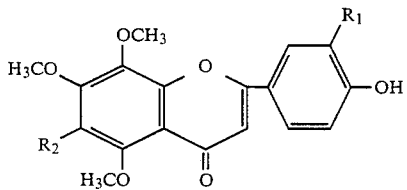

wherein $R_1$ is hydrogen atom or hydroxyl group, $R_2$ is hydroxyl group or methoxyl group or a pharmaceutically acceptable salt of the flavone derivative, and a pharmaceutically acceptable carrier.

DETAILED DESCRIPTION

Though all the dozens of flavone derivatives including the above-mentioned quercitrin obtained by chemical synthesis have a flavone skeleton, there is a large difference in inhibitory activities against AR of the above flavone derivatives depending on the kind and the number of the binding groups such as hydroxyl group, methoxyl group or acetoxyl group, and the binding position.

The compound (II) or the pharmaceutically acceptable salt thereof is a typical example of the inhibitors of AR having the most potent inhibitory activity against AR. LARI-1, LARI-2, LARI-3 and LARI-4 inhibit, respectively, rat lens AR (hereinafter referred to as "RLAR") with the concentrations of inhibitor needed to elicit 50% inhibition (hereinafter referred to as "$IC_{50}$") values of $3.6 \times 10^{-8}M$, $1.6 \times 10^{-7}M$, $2.5 \times 10^{-7}M$ and $3.0 \times 10^{-8}M$, and inhibit, respectively, bovine lens AR (hereinafter referred to as "BLAR") with $IC_{50}$ values of $1.8 \times 10^{-7}M$, $2.9 \times 10^{-7}M$; $4.2 \times 10^{-7}M$ and $1.8 \times 10^{-7}M$, while quercitrin inhibits RLAR and BLAR with $IC_{50}$ values of $4.9 \times 10^{-7}M$ and $3.3 \times 10^{-6}M$, respectively. The inhibitory activities of LARI-1 to 4 are from several to ten times as potent as that of quercitrin.

A process for preparing LARI-1, LARI-2, LARI-3 and LARI-4 being an effective ingredient of the inhibitor of the present invention can be summarized as follows: LARI-1 can be prepared by hydrogenolysis of 3',4',6-tris(benzyloxy)-5,7,8-trimethoxyflavone prepared from pyrogallol employed as a starting material, and LARI-2, LARI-3 and LARI-4 can be prepared according to the method employed for LARI-1. The salts of the above four compounds with Na, K, $NH_4$, Mg, and the like can be easily obtained in a usual manner.

Flavone derivatives such as LARI-1, LARI-2, LARI-3, LARI-4 and the salts thereof have a highly potent inhibitory activity against AR and the inhibitor of the present invention containing the above flavone derivatives as an effective ingredient has an excellent effect on preventing, reducing or treating the complications of diabetes.

The inhibitor of the present invention can be formulated by a usual manner in a form of tablet, powder, syrup and liquid for injections or ophthalmic solutions with conventional pharmaceutical carriers or media and administered both orally and parenterally. Examples of the carrier or medium are, for instance, excipients, binders, lubricants, coloring agents, perfumes, emulsifying agents, dispersing agents, and the like. If necessary, sterilized water, plant oil or harmless organic solvent can be used with the above carrier or medium. Though the usual dosage is 100 mg. or less/kg. body weight/day (on the basis of the amount of a flavone derivative) to an adult, the preferable dosage is determined by physicians according to conditions of patients.

The present invention is more specifically described and explained by means of the following Examples. It is to be understood that the present invention is not limited to the Examples and various changes and modifications may be made in the invention without departing from the spirit and scope thereof.

EXAMPLE 1 [Preparation of 3′,4′-dihydroxy-5,6,7,8-tetramethoxyflavone (LARI-4)]

(1) Preparation of ω-[3,4-bis(benzyloxy)benzoyl]-2-hydroxy-3,4,5,6-tetramethoxyacetophenone To 1.55 g. of 2-hydroxy-3,4,5,6-tetramethoxyacetophenone was added 2.82 g. of 3,4-bis(benzyloxy)benzoyl chloride and 10 ml. of pyridine and heated at 120° C. for 2 hours. The resulting reaction mixture was poured into a mixture of ice and hydrochloric acid and the precipitated oily material was extracted with ether. The ether phase was washed with a diluted hydrochloric acid, an aqueous sodium carbonate solution and water, and then dried. After distilling away ether, the oily residue was dried in a desiccator to give a crude ester.

Into 15 ml. of pyridine was dissolved the obtained ester and added 4 g. of powdered potassium hydroxide. After the resulting mixture was heated at 60° C. for 4 hours with stirring, the reaction mixture was poured into a mixture of water and hydrochloric acid and the precipitated oily material was extracted with ethyl acetate. The ethyl acetate phase was washed with a diluted hydrochloric acid, an aqueous sodium carbonate solution and water, and then dried.

The solvent was distilled away to give 3.16 g. of semisolid crude ω-[3,4-bis(benzyloxy)benzoyl]-2-hydroxy-3,4,5,6-tetramethoxyacetophenone.

(2) Preparation of 3′,4′-bis(benzyloxy)-5,6,7,8-tetramethoxyflavone

Into 15 to 20 ml. of acetic acid was dissolved 2.90 g. of crude -ω[3,4-bis(benzyloxy)benzoyl]-2-hydroxy-3,4,5,6-tetramethoxyacetophenone obtained in Example 1-(1) and added 3 g. of anhydrous sodium acetate. The resulting mixture was refluxed for 4 hours and added water for separating the precipitate. Recrystallization from ethyl acetate yielded 1.46 g. (44% of the theoretical amount) of the desired compound being a colorless needle crystal.

mp: 157° to 157.5° C.

Elementary analysis for $C_{33}H_{30}O_8$ (MW: 554.60): Calcd. (%): C 71.47, H 5.45. Found (%): C 71.33, H 5.27.

(3) Preparation of 3′,4′-dihydroxy-5,6,7,8-tetramethoxyflavone (LARI-4)

Into 200 ml. of a mixed solvent of ethyl acetate and methanol at a ratio of 1:1 was dissolved 1.11 g. of 3′,4′-bis(benzyloxy)-5,6,7,8-tetramethoxyflavone and added 0.2 to 0.3 g. of 10% palladium-charcoal. The resulting mixture was mixed with shaking in a stream of $H_2$ gas until $H_2$ absorption was completed. After filtering out the catalyst, the obtained filtrate was concentrated. The residue was recrystallized from methanol to give 0.74 g. (97% of the theoretical amount) of the desired compound being a colorless prismatic crystal.

mp: 223° to 225° C. (decompose)

Elementary analysis for $C_{19}H_{18}O_8$ (MW: 374.35): Calcd. (%): C 60.96, H 4.85. Found (%): C 61.18, H 4.78.

EXAMPLE 2

[Preparation of 3′,4′,6-trihydroxy-5,7,8-trimethoxy-flavone (LARI-1)]

(1) Preparation of 5-benzyloxy-ω-[3,4-bis(benzyloxy)benzoyl]-2-hydroxy-3,4,6-trimethoxyacetophenone The procedure of Example 1-(1) was repeated except that 3.2 g. of 5-benzyloxy-2-hydroxy-3,4,6-trimethoxyacetophenone and 5.5 g. of 3,4-bis(benzyloxy)benzoyl chloride were employed as the starting materials. Recrystallization from ethyl acetate-methanol yielded 4.5 g. (72% of the theoretical amount) of the desired compound being a yellowish columnar crystal.

mp: 123° to 125° C.

Elementary analysis for $C_{39}H_{36}O_9$ (MW: 648.72): Calcd. (%): C 72.21, H 5.59. Found (%): C 71.90, H 5.79.

(2) Preparation of 3′,4′,6-tris(benzyloxy)-5,7,8-trimethoxyflavone

The procedure of Example 1-(2) was repeated except that 3.24 g. of 5-benzyloxy-ω-[3,4-bis(benzyloxy)benzoyl]-2-hydroxy-3,4,6-trimethoxyacetophenone obtained in Example 2-(1) was employed as the starting material. Recrystallization from ethyl methyl ketone yielded 2.84 g. (90% of the theoretical amount) of the desired compound being a colorless needle crystal.

mp: 155° to 156° C.

Elementary analysis for $C_{39}H_{34}O_8$ (MW: 630.70): Calcd. (%): C 74.27, H 5.43. Found (%): C 74.50, H 5.39.

(3) Preparation of 3′,4′,6-trihydroxy-5,7,8-trimethoxyflavone (LARI-1)

The procedure of Example 1-(3) was repeated except that 2.21 g. of 3′,4′,6-tris(benzyloxy)-5,7,8-trimethoxyflavone obtained in Example 2-(2) was employed as the starting material. Recrystallization from ethyl acetate-methanol yielded 1.14 g. (90% of the theoretical amount) of the desired compound being a light yellowish needle crystal.

mp: 279° to 281° C.

Elementary analysis for $C_{18}H_{16}O_8$ (MW: 360.33): Calcd. (%): C 60.00, H 4.48. Found (%): C 60.01, H 4.62.

EXAMPLE 3

[Preparation of 4′-hydroxy-5,6,7,8-tetramethoxyflavone (LARI-2)]

(1) Preparation of ω-(4-benzyloxy)benzoyl-2-hydroxy-3,4,5,6-tetramethoxyacetophenone The procedure of Example 1-(1) was repeated except that 1.55 g. of 2-hydroxy-3,4,5,6-tetramethoxyacetophenone and 2.15 g. of 4-(benzyloxy)benzoyl chloride were employed as the starting materials to give 2.62 g. of the crude desired compound.

(2) Preparation of 4′-benzyloxy-5,6,7,8-tetramethoxyflavone

The procedure of Example 1-(2) was repeated except that 2.50 g. of crude ω-(4-benzyloxy)-5,6,7,8-tetramethoxyacetophenone obtained in Example 3-(1) was employed as the starting material. Recrystallization from water-methanol yielded 1.37 g. of the desired compound being a colorless needle crystal.

mp: 132° to 134° C.

Elementary analysis for $C_{26}H_{24}O_7$ (MW: 448.48): Calcd. (%): C 69.63, H 5.39. Found (%): C 69.78, H 5.34.

(3) Preparation of 4'-hydroxy-5,6,7,8-tetramethoxyflavone (LARI-2)

The procedure of Example 1-(3) was repeated except that 1.08 g. of 4'-benzyloxy-5,6,7,8-tetramethoxyflavone obtained in Example 3-(2) was employed as the starting material. Recrystallization from water-methanol yielded 0.86 g. (96% of the theoretical amount) of the desired compound being a colorless needle crystal.
mp: 187° to 188.5° C.
Elementary analysis for $C_{19}H_{18}O_7$ (MW: 358.35): Calcd. (%): C 63.68, H 5.06. Found (%): C 63.88, H 4.96.

EXAMPLE 4

[Preparation of 4',6-dihydroxy-5,7,8-trimethoxyflavone (LARI-3)]

(1) Preparation of 5-benzyloxy-ω-(4-benzyloxy)benzoyl-2-hydroxy-3,4,6-trimethoxyacetophenone The procedure of Example 1-(1) was repeated except that 3.32 g. of 5-benzyloxy-2-hydroxy-3,4,6-trimethoxyacetophenone and 3.50 g. of 4-(benzyloxy)benzoyl chloride were employed as the starting materials. Recrystallization from ethyl acetate-methanol yielded 3.36 g. (62% of the theoretical amount) of the desired compound being a yellowish needle crystal.
mp: 102° to 103° C.
Elementary analysis for $C_{32}H_{30}O_8$ (MW: 542.59): Calcd. (%): C 70.83, H 5.57. Found (%): C 70.62, H 5.61.

(2) Preparation of 4',6-bis(benzyloxy)-5,7,8-trimethoxyflavone

The procedure of Example 1-(2) was repeated except that 2.98 g. of 5-benzyloxy-ω-(4-benzyloxy) benzoyl-2-hydroxy-3,4,6-trimethoxyacetophenone obtained in Example 4-(1) was employed as the starting material. Recrystallization from ethyl methyl ketone yielded 2.60 g. (90% of the theoretical amount) of the desired compound being a colorless needle crystal.
mp: 172° to 173° C.
Elementary analysis for $C_{32}H_{28}O_7$ (MW: 524.57): Calcd. (%): C 73.27, H 5.38. Found (%): C 73.55, H 5.52.

(3) Preparation of 4',6-dihydroxy-5,7,8-trimethoxyflavone (LARI-3)

The procedure of Example 1-(3) was repeated except that 2.36 g. of 4',6-bis(benzyloxy)benzoyl-5,7,8-trimethoxyflavone obtained in Example 4-(2) was employed as the starting material. Recrystallization from ethyl acetate-methanol yielded 1.26 g. (81% of the theoretical amount) of the desired compound being a colorless needle crystal.
mp: 266° to 268° C.
Elementary analysis for $C_{18}H_{16}O_7$ (MW: 344.33): Calcd. (%): C 62.79, H 4.68. Found (%): C 62.85, H 4.80.

RECIPE EXAMPLE

The inhibitory activities against AR of LARI-1, LARI-2, LARI-3 and LARI-4 were determined according to the following method. As reference examples, there were employed quercitrin and two flavone derivatives having a relatively similar structure to those of the above compounds, i.e. 4',6-dihydroxy-3',5,7,8 tetramethoxyflavone and 4',5-dihydroxy-3',6,7,8-tetramethoxyflavone (hereinafter referred to as "Ref-1" and "Ref-2", respectively).

In Recipe Example, the followings were used. NADPH was purchased from the Oriental Yeast Co., Ltd. DL-Glyceraldehyde and quercitrin were purchased from Nakarai Chemicals, Ltd. DEAE-Sephacel and Sephadex G-75 were purchased from Pharmacia Fine Chemicals. Matrex gel red A was purchased from the Amicon Co. All other chemicals were of the highest grade commercially available.

(1) Materials

Rat lenses were removed from eyes of rats of the Wistar strain weighing 200 to 250 g. Bovine eyes were obtained from a local abattoir, and the lenses were removed and frozen until needed.

(2) Preparation of Inhibitor solution

All compounds were dissolved in propylene glycol being a useful solvent of low toxicity for some water-insoluble drugs. Usually a $10^{-3}$M solution was prepared and diluted to the desired concentrations with propylene glycol. To the reaction mixture were added aliquots of the diluted solution to yield concentrations of $10^{-8}$M to $10^{-5}$M and a propylene glycol concentration of 1%.

(3) Assay of AR activity

AR assays were conducted according to the procedure of Hayman and Kinoshita (J. Biol. Chem. 240, p. 877 (1965)), except for the addition of ammonium sulfate instead of lithium sulfate to the reaction mixture. Assays were performed at 30° C. in 0.1M sodium phosphate buffer (pH 6.2) containing 0.4M ammonium sulfate, 10 mM DL-glyceraldehyde, 0.16 mM NADPH and the enzyme (0.010 to 0.016 unit) in a total volume of 1.0 ml. The effects of inhibitors on the enzyme activity were determined in the reaction mixture containing 10 μl. of each inhibitor solution at the desired concentrations. The blank reference to correct for non-specific reduction of NADPH contained all of the above compounds except DL-glyceraldehyde. The reaction was initiated by the addition of DL-glyceraldehyde, and the rate of NADPH oxidation was followed by recording the decrease in absorbance at 340 nm on a Gilford model 250 spectrophotometer.

(4) Purification of lens AR

BLAR and RLAR were purified according to the method of Inagaki et al (Archs Biochem. Biophys. 216, p. 337 (1982)). Briefly, a 40 to 75% ammonium sulfate fraction was subjected to chromatography on DEAE-Sephacel, followed by two column chromatographic steps, i.e. affinity chromatography using Matrex gel red A and gel filtration on Sephadex G-75. In the procedure, a key step was affinity chromatography on Matrex gel red A. BLAR adsorbed on the gel was eluted with 0.33 mM NADPH, and elution of RLAR adsorbed on the gel was effected by means of a linear gradient of NaCl (0 to 1.0 M). BLAR and RLAR were purified over 12,000-fold (4.8 units/mg. protein) and 380-fold (4.7 units/mg. protein), respectively, and used for determining $IC_{50}$ values.

(5) Determination of $IC_{50}$

The concentration of inhibitor required for eliciting a 50% inhibition ($IC_{50}$) was determined according to the method of Kador et al (Docum. Ophthal. Proc. Series 18, p. 117 (1979)).

The results are shown in Table 1 and Table 2.

TABLE 1

| | Inhibition against enzyme activity (%) | | | | | |
|---|---|---|---|---|---|---|
| | RLAR | | | BLAR | | |
| Compound | $10^{-5}$M | $10^{-6}$M | $10^{-7}$M | $10^{-5}$M | $10^{-6}$M | $10^{-7}$M |
| LARI-1 | 96 | 92 | 73 | 100 | 91 | 35 |

TABLE 1-continued

| | Inhibition against enzyme activity (%) | | | | | |
| --- | --- | --- | --- | --- | --- | --- |
| | RLAR | | | BLAR | | |
| Compound | $10^{-5}$M | $10^{-6}$M | $10^{-7}$M | $10^{-5}$M | $10^{-6}$M | $10^{-7}$M |
| LARI-2 | 91 | 81 | 44 | 94 | 80 | 24 |
| LARI-3 | 92 | 74 | 36 | 95 | 70 | 18 |
| LARI-4 | 97 | 93 | 78 | 100 | 90 | 37 |
| Ref-1 | 58 | 22 | 6 | 63 | 19 | 0 |
| Ref-2 | 40 | 15 | 0 | 56 | 19 | 0 |
| quercitrin | 84 | 56 | 38 | 66 | 32 | 0 |

TABLE 2

| | $IC_{50}$ (M) $\times 10^6$ | |
| --- | --- | --- |
| Compound | RLAR | BLAR |
| LARI-1 | 0.036 | 0.18 |
| LARI-2 | 0.16 | 0.29 |
| LARI-3 | 0.25 | 0.42 |
| LARI-4 | 0.030 | 0.18 |
| quercitrin | 0.49 | 3.3 |

It is clear from the results of Tables 1 and 2 that the flavone derivatives being an effective ingredient of the inhibitor of the present invention have highly potent inhibitory activities against AR comparing with the other flavone derivatives including quercitrin.

What we claim is:

1. A pharmaceutical composition having an inhibitory activity against aldose reductase which comprises, as the effective ingredient, a flavone derivative having the following formula (II):

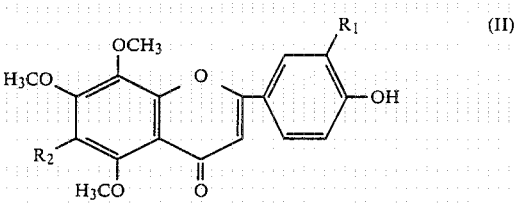

wherein $R_1$ is a hydrogen atom or a hydroxyl group, $R_2$ is a hydroxyl group or a methoxyl group or a pharmaceutically acceptable salt of said flavone derivative, with the proviso that when $R_1$ is hydrogen, $R_2$ is not a methoxyl group, and a pharmaceutically acceptable carrier.

2. A method of inhibiting aldose reductase which comprises administering an effective amount of a pharmaceutical composition having an inhibitory activity against aldose reductase, said composition having as the effective ingredient, a flavone derivative having the following formula (II):

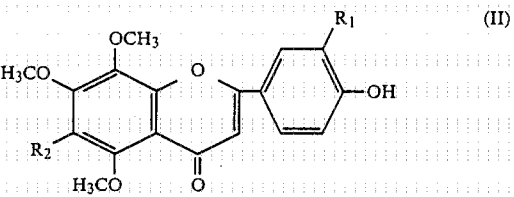

wherein $R_1$ is a hydrogen atom or a hydroxyl group, $R_2$ is a hydroxyl group or a methoxyl group or a pharmaceutically acceptable salt of said flavone derivative, to a patient requiring such treatment.

* * * * *